United States Patent [19]

Weiss et al.

[11] 4,252,786

[45] Feb. 24, 1981

[54] CONTROLLED RELEASE TABLET

[75] Inventors: Aaron L. Weiss, E. Brunswick, N.J.; Richard W. Walton, Langhorne, Pa.; Albert E. de Lorimier, E. Brunswick, N.J.

[73] Assignee: E. R. Squibb & Sons, Inc., Princeton, N.J.

[21] Appl. No.: 95,036

[22] Filed: Nov. 16, 1979

Related U.S. Application Data

[63] Continuation of Ser. No. 621,136, Oct. 10, 1975, abandoned.

[51] Int. Cl.$^3$ ............... A61K 9/22; A61K 9/24; A61K 9/32; A61K 9/36
[52] U.S. Cl. ............... 424/19; 424/21; 424/22; 424/32; 424/33; 424/35
[58] Field of Search ............... 424/14–22, 424/31–35

[56] References Cited

U.S. PATENT DOCUMENTS

| | | | |
|---|---|---|---|
| 2,887,440 | 5/1969 | Greminger et al. | 424/35 X |
| 3,096,248 | 7/1963 | Rudzki | 424/35 X |
| 3,247,066 | 4/1966 | Milosovich | 424/20 X |
| 3,388,041 | 6/1968 | Gans et al. | 424/35 X |
| 3,400,185 | 9/1968 | Kohnle et al. | 424/33 X |
| 3,458,622 | 7/1969 | Hill | 424/19 |
| 3,538,214 | 11/1970 | Polli et al. | 424/19 |
| 3,632,739 | 1/1972 | Kornblum | 424/19 |
| 3,835,221 | 9/1974 | Fulberth et al. | 424/20 |
| 3,907,983 | 9/1975 | Seth | 424/35 |
| 3,917,813 | 11/1975 | Pedersen | 424/20 |
| 4,140,756 | 2/1979 | Gallian | 424/21 |

*Primary Examiner*—Shep K. Rose
*Attorney, Agent, or Firm*—Lawrence S. Levinson; Donald J. Barrack

[57] ABSTRACT

The rate of release of medicament from a controlled release tablet having a polymeric vinylpyrrolidonecarboxyvinyl hydrophilic core is improved by coating the medicament-containing core with a substantially insoluble rupturable film which is water permeable.

20 Claims, No Drawings

CONTROLLED RELEASE TABLET

This is a continuation of application Ser. No. 621,136, filed Oct. 10, 1975, now abandoned.

BACKGROUND OF THE INVENTION

A controlled release tablet for the administration of medicinal agents over a prolonged period of up to about eight hours is described in U.S. Pat. No. 3,458,622, July 29, 1969, to John A. Hill. This patent discloses a compressed tablet for the prolonged release of a medicament containing that medicament in a core formed from a polymeric vinyl pyrrolidone, preferably polyvinyl pyrrolidone (PVP), and a carboxyvinyl hydrophilic polymer such as those marketed under the trademark Carbopol. The core material formed from the two polymeric substances provides the controlled release effect by forming a complex under the action of water or gastric fluid. This complex is gel-like in consistency and retards the diffusion of active ingredient from the tablet.

It has been found, however, that there is a tendency for an initial surge of medicament to occur so that the first amount of drug released may be larger than subsequently. This may be due to the short delay until water or gastric fluid acts on the polymeric blend and the gel, which provides the delaying action, forms.

It is therefore an object of this invention to improve the characteristics of controlled release tablets formed from a blend of polymers such as those in the Hill patent referred to above by reducing the tendency for an initial surge in the release of medicament.

SUMMARY OF THE INVENTION

This invention relates to an improved controlled release tablet for medicaments comprising an active ingredient which is dispersed in a water soluble permeable matrix. The improvement comprises coating the delayed release matrix with a rupturable film, which is water permeable and substantially insoluble in water, comprising a combination of hydrophobic and hydrophilic polymers. More particularly, this invention relates to an improved release tablet for the timed release of medicament having a core containing the medicament formed from a blend of polymeric vinyl pyrrolidone and a carboxyvinyl hydrophilic polymer and coated with a relatively insoluble, water permeable, rupturable film comprising a combination of hydrophobic and hydrophilic polymers.

DETAILED DESCRIPTION OF THE INVENTION

This invention concerns a controlled release drug tablet formulation and involves the application of a film comprising a combination of hydrophobic and hydrophilic polymers to an insoluble swelling type delayed release matrix to modify the drug release rate.

In the water-insoluble matrix of the type described in the Hill patent referred to above, the controlled release rate of the drug is dependent upon the interaction of the two principal ingredients, the polymer and the hydrocolloid, in the presence of water to form a gummy complex of low solubility. Since little of the gummy complex is present initially, the drug at or near the surface dissolves fairly rapidly and there is an initial surge wherein a relatively large amount of drug is released in the beginning for a period of about one hour. As the colloid complex is formed, once aqueous solution penetrates the surface of the tablet, the gel retards the dissolution of the drug out of the tablet.

According to this invention, the delayed release characteristics of a water insoluble matrix of the type described in the Hill patent is improved by coating such a matrix with a film of the kind described below. Initially, while the film is intact, the release of the drug contained in the matrix is primarily controlled by diffusion of solvent and solute molecules through the film. As water or gastric fluid permeates through the film, the gummy complex forms and the slight swelling of the complex causes the film to rupture or erode. The release rate is then controlled by the gummy complex. The application of a relatively water insoluble, water permeable film primarily controls the drug release rate while the matrix gel is being generated and a smoother, gradual, more uniform release rate is achieved during the entire period of about eight to twelve hours, approaching a zero order release pattern. The release pattern of the core, upon application of the film, can be varied over a range by varying the composition and amount of film-forming mixture.

The controlled release tablets are prepared, according to this invention, by forming a tablet-like matrix in which the active ingredient is dispersed and then coating this matrix with a water permeable film of low water solubility. The film is a combination of hydrophobic polymer which is slightly soluble in water and hydrophilic polymer which is water soluble. When combined, they constitute a relatively insoluble blend.

The matrix comprises a polymer blend. One component of the polymer blend is a vinyl polymer, e.g., polyvinyl pyrrolidone (Merck Index, 8th ed., 1968, page 849) having a molecular weight of about 5000 to 80,000, preferably about 40,000, generally referred to as PVP. The second component of the polymer blend is a carboxypolymethylene hydrocolloid polymer of the type described in U.S. Pat. No. 2,909,462, Oct. 10, 1959 [see also Chem. Eng. News 36, No. 39, page 64 (Sept. 29, 1958)], a carboxyvinyl hydrophilic polymer of acrylic acid cross-linked with polyalkenyl polyether and having active carboxyl groups, particularly acrylic acid cross-linked with polyallyl sucrose. Such carboxyvinyl hydrophilic polymers are marketed under the trademark Carbopol with designations 934, 940 941 by B. F. Goodrich Chemical Co.

Controlled release of the medicament from tablet matrices formed from such polymer blends can be achieved with relatively small proportions of the release controlling substances. In general, the polymer blend comprises less than 50% by weight of the matrix and, indeed, weight of the complete tablet. The proportions by weight of the two polymeric substances in the blend which forms the matrix is about 1:10 to 10:1 (by weight) of vinyl polymer to carboxypolymethylene polymer. The preferred ratio is about 1:1 to 1.5:1. The ratio (by weight) of carboxyvinyl polymer to active drug ingredient is less than 0.5:1, preferably about 0.1 to 0.45:1. The combined weight of the two polymers in the blend may exceed half the weight of active medicament, but is preferably below about 75% of the weight of active drug. These proportions refer to the matrix.

Finished tablets having a total weight of up to about 1 gm. can be prepared. Of this total weight, the coating described in detail below comprises about 5 to 15%.

Thus the controlled release tablet matrix preferably comprises a blend of an effective amount of medicament which is preferably at least about 50% of the total matrix weight, vinyl polymer, preferably PVP, and a carboxyvinyl hydrophilic polymer of acrylic cross-linked with polyalkenyl polyether, preferably a polymer of acrylic acid cross-linked with polyallyl sucrose and especially Carbopol. The release control substance is a gel formed by the interaction of the polymers in the presence of water.

The ratio by weight of vinyl polymer to carboxypolymethylene polymer is about 1:10 to 10:1, preferably about 1:1. The ratio by weight of carboxyvinyl polymer to active drug ingredient is less than 0.5:1, preferably about 0.1 to 0.45:1. The combined weight of the polymers is below about 75% of the weight of the active drug ingredient.

To form the tablet matrix or core, a dry granulation technique is preferred. All of the ingredients are blended in dry form, made more dense by slugging or compaction and reducing to a granulation by grinding. The ground particles are then compressed into tablet form which can take any of the conventional shapes, e.g., round, elongated, oval, etc. A tablet press fitted with suitably sized punches and dies are used to form a tablet core of any desired weight, shape and composition.

In carrying out the dry granulation procedure various other conventional ingredients can be included as required. For example, a diluent or filler may be included for weight adjustment. Such diluents include, for example, lactose, mannitol, corn starch, particularly, various cellulose derivatives such as wood cellulose (Solkafloc) and especially microcrystalline cellulose marketed under the trademark Avicel (see U.S. Pat. Nos. 2,978,446 and 3,141,875). Other additives may include lubricants like stearic acid, palmitic acid, magnesium stearate, calcium stearate, talc, carnauba wax or the like. Silica flow conditioners or glidants may also be included. Colors acceptable in drugs such as the various F.D. & C. colors can be added at various stages, including spray coatings of the finished core.

As an alternative, though not preferred, the wet granulation technique can also be used. According to this procedure, the dry active ingredient, vinyl polymer and polymethylene polymer and other diluents are blended, for example, in a planetary mixer. The powders are wetted with a granulating liquid like methylene chloride, chloroform, methyl chloroform, pure or denatured ethyl alcohol, isopropyl alcohol, 1,1-dichloroethane, 1,2-dichloroethane, 1,1,1-trichloroethane or the like. Binders such as zein, ethyl cellulose, beta-pinene polymers, gelatin, shellac or the like may be included in the granulating liquid. The moist mass is granulated, e.g., by forcing through a screen of suitable mesh size, dried, and, if desired, the particles further reduced in size. The granulate is then compressed in conventional manner, using lubricants, glidants, etc., as required.

When the tablet matrix has been formed and, optionally the color has been applied, a film is applied according to this invention. The film comprises a combination of hydrophobic and hydrophilic polymers which permits the entry of water and hydration of the matrix so that there is not a large initial surge in the release of medicament.

The hydrophilic polymers are water soluble polymers (under pH 5.5). They include cellulose methyl ethers like methyl cellulose, hydroxypropylmethyl cellulose, hydroxymethyl cellulose phthalate, also hydroxypropyl cellulose, cellulose acetate phthalate or polyvinyl alcohol.

The hydrophobic polymers are slightly soluble in water. (By slightly soluble is meant the definition in USP XIX, page 6, although polymers up to 3% soluble in water can be used.) They include cellulose ethyl esters like ethyl cellulose, also cellulose acetate, polyvinyl alcohol-maleic anhydride copolymers, β-pinene polymers (Piccolyte), glycerol esters of wood resins like glycerol ester of partially dimerized rosin, glycerol ester of partially hydrogenated wood rosin, glycerol ester of polymerized rosin, hydroxypropyl methyl cellulose phthalate, etc.

Preferred are combinations of methyl cellulose and ethyl cellulose or hydroxypropylmethyl cellulose and ethyl cellulose.

One or more members of each class of polymer can be used. The proportion of hydrophilic polymer or polymers to hydrophobic polymer or polymers is within the range of about 4:1 to about 1:4 (by weight) preferably about 1.5:1 to 1:1. These polymers are best combined in a proportion which results in rupture in about one hour. A film of about 1 to 15 mil. (0.001 to 0.015 inches) preferably 3 to 7 mil., in thickness is sufficient to achieve the purpose.

The film formers are applied by spraying a system containing them on the core by conventional film coating techniques. The film formers are dissolved in a solvent or mixture of solvents in which both types are soluble or form a solvent. Such solvents include alcohols like methyl alcohol, ethyl alcohol or isopropyl alcohol, ketones like acetone, methyl ethyl ketone, chlorinated hydrocarbons like methylene chloride, dichloroethane, 1,1,1-trichloroethane, etc. Preferred are methylene chloride plus isopropyl alcohol or methylene chloride plus methyl alcohol (preferably 70%:30%).

The film forming composition may optionally include plasticizers such as triethyl citrate, diethyl phthalate, propylene glycol, glycerin, butyl phthalate, castor oil or the like to provide the desired balanced characteristics. Preferably, the color, if used, is applied in this film coating composition. These colors include F.D. & C. approved colors or lakes. Opacifiers such as titanium dioxide can also be included.

A wide variety of medicaments which are orally administered in tablet form can be used in the form of tablets prepared according to this invention. These include, for example, adrenergic agents such as ephedrine, desoxyephedrine, phenylephrine, epinephrine and the like, cholinergic agents such as physostigmine, neostigmine and the like, antispasmodic agents such as atropine, methantheline, papaverine and the like, curariform agents such as chlorisondamine and the like, tranquilizers and muscle relaxants such as fluphenazine, chlorpromazine, triflupromazine, mephenesin, meprobamate and the like, antidepressants like amitriptyline, nortriptyline, and the like, antihistamines such as diphenhydramine, dimenhydrinate, tripelennamine, perphenazine, chlorprophenazine, chlorprophenpyridamine and the like, hypotensive agents such as rauwolfia, reserpine and the like, cardioactive agents such as bendroflumethiazide, flumethiazide, chlorothiazide, aminotrate, propranolol, procainamide and the like, steroids such as testosterone, prednisolone, and the like, antibacterial agents, e.g., sulfonamides such as sulfadiazine, sulfamerazine, sulfamethazine, sulfisoxazole and the like, antimalarials such as chloroquine and the like, antibiotics such as the tetracyclines, nystatin, streptomycin, cephradine and other cephalosporins, penicillin, semi-synthetic penicillins, griseofulvin and the like, sedatives such as chloral hydrate, phenobarbital and other barbiturates, glutethimide, antitubercular agents such as isoniazid and the like, analgesics such as aspirin, propoxyphene, meperidine and the like, etc. These substances are frequently employed either as the free compound or in a salt form, e.g., acid addition salts, basic salts like alkali metal salts, etc. Other therapeutic agents having the same or different physiological activity can also be employed in pharmaceutical preparations within the scope of the present invention.

The invention is particularly adapted for controlled release tablets containing the antiarrhythmic agent procainamide (usually formulated in the form of its hydrochloride).

The following examples are illustrative of the invention and constitute preferred embodiments. They also serve as models for additional compositions within the scope of the invention.

EXAMPLE 1

The following ingredients are used to make 1000 tablets each containing 500 mg. of procainamide hydrochloride:

| A. Compressed Tablet | |
|---|---|
| Procainamide HCl | 500 gm. |
| Polyvinylpyrrolidone (pharmaceutical grade) | 144 gm. |
| Carbopol 934 (carboxypolymethylene polymer) | 96 gm. |
| Avicel (microcrystalline cellulose) | 23.4 gm. |
| Carnauba wax (U.S. Pat. No. 1 yellow powdered, 100 mesh) | 15.6 gm. |
| Stearic acid (food grade) | 7.8 gm. |
| Syloid 244 Grade 68 (silica glidant) | 3.95 gm. |

| B. Coating Solution | Per Liter |
|---|---|
| Methocel 60 HG 15 cps. (hydroxpropymethyl cellulose) | 30 gm. |
| Ethyl cellulose | 20 gm. |
| Triethyl Citrate | 2 gm. |
| Isopropyl Alcohol 99% (30% v/v of solvent) | 284.4 ml. |

All of the ingredients under A above, except the stearic acid and Syloid are blended in the dry form. The dry blend is compacted on a tablet press then reduced by grinding to about 20 mesh. The stearic acid lubricant and glidant are added to the dry granulate and blended thoroughly. The mixture is then compressed on a tablet press to form biconvex oval tablet matrices with slightly flattened ends weighing 790 mg. each.

The coating solution B is then applied to the tablet matrices by airless spray in a back outlet rotary coating pan. The coating is applied until a 3.5 to 4 mil. coating is obtained.

EXAMPLE 2

Tablet matrices are prepared as described in Example 1.

A color coat solution is prepared by adding 400 ml. of Opaspray Yellow (a dispersion of F.D. & C. yellow #5 & 6 lakes, titanium oxide and hydroxypropylmethyl cellulose in SD3A Alcohol) to the coating solution B in Example 1 and mixing. The compressed tablet matrices are then sprayed as in Example 1 to obtain yellow coated tablets each weighing a total of 840 mg. and containing 500 mg. of procainamide HCl (core=791 mg.).

EXAMPLE 3

The following ingredients are used to make 1000 tablets each containing 570 mg. of cephradine:

| A. Compressed Tablet | |
|---|---|
| Cephradine | 570.6 gm. |
| Lactose anhydrous | 274.4 gm. |
| Plasdone (PVP) K-30 | 60.0 gm. |
| Carbopol 934 | 40.0 gm. |
| Ethyl cellulose | 6.0 gm. |
| Talc | 39.7 gm. |
| Emersol | 9.3 gm. |
| Methylene chloride | qs. |

| B. Coating Solution | Per Liter |
|---|---|
| Hydroxypropylmethylcellulose phthalate (XD-55) | 50 gm. |
| Methocel 60 HG premium 15 cps. | 25 gm. |
| Methanol ca 12.5% q.s. | |
| Isopropyl Alcohol 15% q.s. | |
| Methylene chloride ca 65% q.s. | |

The cephradine, lactose, Plasdone and Carbopol are mixed. The mixture is granulated with the ethyl cellulose and methylene chloride. The granulation is dried and reduced to 20 mesh size. The talc and Emersol are added and the mixture is compressed into tablets (1000). The coating solution is well mixed and sprayed onto the compressed cores to a thickness of 3-4.5 mil.

EXAMPLE 4

The release rate of active drug determined for the uncoated cores and the film coated tablets prepared according to Example 1 by the U.S.P. XIX dissolution method (p.651) using 1 liter of water at 37° C. with the basket rotated at 50 rpm. is as follows:

TABLE I

| | % Procainamide Released Per Hour | |
|---|---|---|
| Hour | Film Coated Tablet | Uncoated Core |
| 1 | 14.6% | 40.0% |
| 2 | 20.1 | 11.8 |
| 3 | 13.3 | 14.4 |
| 4 | 20.0 | 9.8 |
| 5 | 1.5 | 3.6 |
| 6 | 6.3 | 3.2 |
| 7 | 5.7 | 3.0 |
| 8 | 2.1 | 0 |
| 9–10 | 9.9 | 6.1 |

EXAMPLE 5

The release rate of cephradine determined for the coated tablets of Example 3 is as follows:

TABLE II

| | % Cephradine Released Per Hour |
|---|---|
| Hour | Percent |
| 1 | 26 |
| 2 | 15 |
| 3 | 12 |
| 4 | 10 |
| 5 | 9 |
| 6 | 8 |

What is claimed is:

1. A film coated controlled release medicinal tablet comprising:
   (i) a compressed matrix comprising an effective amount of medicament dispersed in a blend of 1:10 to 10:1 parts by weight polymeric vinyl pyrrolidone and a carboxyvinyl hydrophilic polymer; and
   (ii) a substantially water insoluble, water permeable film coating on the compressed matrix, the film coating having a thickness of about 1 to 15 mil. and comprising a blend of hydrophobic polymer selected from the group consisting of cellulose ethyl esters, cellulose acetate, polyvinyl alcohol-maleic anhydride copolymers, β-pinene polymers, glycerol esters of wood resins, and hydroxypropyl methyl cellulose phthalate, and hydrophilic polymer selected from the group consisting of cellulose methyl ethers, hydroxypropyl cellulose, cellulose acetate phthalate and polyvinyl alcohol, wherein the weight ratio of hydrophilic polymer to hydrophobic polymer is within the range of about 4:1 to about 1:4; wherein the release rate of medicament is initially controlled primarily by the film coating and after rupture or erosion of the film the release rate of medicament is controlled by the compressed matrix; and wherein the release of the medicament through the film begins within about one hour after the tablet has been ingested.

2. A tablet as in claim 1 wherein the compressed matrix comprises an effective amount of medicament which is at least 50% of the total tablet weight dispersed in a polymer blend comprising 1:10 to 10:1 parts by weight of polyvinyl pyrrolidone and polymer of acrylic acid cross-linked with polyallyl sucrose.

3. A tablet as in claim 1 wherein the hydrophobic polymer is ethyl cellulose and the hydrophilic polymer is methyl cellulose.

4. A tablet as in claim 1 wherein the hydrophobic polymer is ethyl cellulose and the hydrophilic polymer is hydroxypropylmethyl cellulose.

5. A tablet as in claim 1 wherein the matrix comprises polyvinyl pyrrolidone and a carboxyvinyl hydrophilic polymer of acrylic acid cross-linked with polyalkenyl polyether and the film coating comprises ethyl cellulose and hydroxypropylmethyl cellulose.

6. A tablet as in claim 1 wherein the matrix comprises polyvinyl pyrrolidone and a carboxyvinyl hydrophilic polymer of acrylic acid cross-linked with polyalkenyl polyether and the film coating comprises ethyl cellulose and methyl cellulose.

7. A tablet as in claim 1 wherein the medicament is procainamide or salt thereof.

8. A tablet as in claim 1 wherein the medicament is cephradine.

9. A tablet as in claim 1 wherein the matrix comprises medicament, polyvinyl pyrrolidone and polymer of acrylic acid cross-linked with polyallyl sucrose and the film coating comprises ethyl cellulose and hydroxypropylmethyl cellulose.

10. A tablet as in claim 1 wherein the matrix comprises medicament, polyvinyl pyrrolidone and polymer of acrylic acid cross-linked with polyallyl sucrose and the film coating comprises ethyl cellulose and methyl cellulose.

11. A tablet as in claim 10 wherein the medicament is procainamide or salt thereof.

12. A tablet as in claim 1 wherein the film is about 3 to 7 mil. in thickness.

13. A tablet as in claim 1 wherein the ratio of hydrophilic polymer to hydrophobic polymer is about 1.5:1 to 1:1 and the film is about 3 to 7 mil. in thickness.

14. A tablet as in claim 2 wherein the medicament is procainamide or salt thereof.

15. A tablet as in claim 2 wherein the hydrophobic polymer is ethyl cellulose and the hydrophilic polymer is methyl cellulose.

16. A tablet as in claim 2 wherein the hydrophobic polymer is ethyl cellulose and the hydrophilic polymer is hydroxypropylmethyl cellulose.

17. A tablet as in claim 2 wherein the medicament is procainamide hydrochloride, the hydrophobic polymer is ethyl cellulose and the hydrophilic polymer is hydroxypropylmethyl cellulose.

18. A tablet as in claim 14 wherein the ratio of hydrophilic polymer to hydrophobic polymer is about 1.5:1 to 1:1 and the film is about 3 to 7 mil. in thickness.

19. A tablet as in claim 2 wherein said polymer blend comprises polyvinyl pyrrolidone and polymer of acrylic acid cross linked with polyallyl sucrose in a ratio of about 1.5:1, the ratio of said last named polymer to said medicament is about 0.1 to 0.45:1, said water soluble hydrophilic polymer is hydroxypropylmethylcellulose and said slightly water soluble hydrophobic polymer is ethyl cellulose in a ratio of about 1:1 to 1.5 to 1 and said film is about 3 to 7 mil. in thickness and comprises about 5 to 15% of finished tablet weight.

20. A tablet as in claim 19 wherein the medicament is procainamide hydrochloride.

* * * * *

UNITED STATES PATENT AND TRADEMARK OFFICE
CERTIFICATE OF CORRECTION

PATENT NO. : 4,252,786

DATED : February 24, 1981

INVENTOR(S) : Aaron L. Weiss, et al.

It is certified that error appears in the above-identified patent and that said Letters Patent are hereby corrected as shown below:

In column 1, line 4, the serial no. should read --621,316--

In Example 1, under the description of the coating solution the following has been omitted after the last ingredient:

--Methylene Chloride    q.s. 1 liter (ca. 664 ml.)--

Signed and Sealed this

Thirteenth Day of October 1981

[SEAL]

Attest:

Attesting Officer

GERALD J. MOSSINGHOFF

Commissioner of Patents and Trademarks